(12) United States Patent
Lerousseau et al.

(10) Patent No.: US 12,308,126 B1
(45) Date of Patent: May 20, 2025

(54) DEVICE AND METHOD FOR PREDICTING A RELAPSE OF A CANCER FOR A PATIENT

(71) Applicants: INSTITUT CURIE, Paris (FR); INSTITUT NATIONAL DE LA SANTE ET DE LA RECHERCHE MEDICALE, Paris (FR); ECOLE NATIONALE SUPERIEURE DES MINES DE PARIS, Paris (FR); UNIVERSITE DE VERSAILLES-SAINT-QUENTIN-EN-YVELINES, Versailles (FR)

(72) Inventors: Marvin Lerousseau, Paris (FR); Thomas Walter, Paris (FR); Anne Vincent-Salomon, Paris (FR); François-Clément Bidard, Paris (FR)

(73) Assignees: INSTITUT CURIE, Paris (FR); INSTITUT NATIONAL DE LA SANTE ET DE LA RECHERCHE MEDICALE, Paris (FR); ECOLE NATIONALE SUPERIEURE DES MINES DE PARIS, Paris (FR); UNIVERSITE DE VERSAILLES-SAINT-QUENTIN-EN-YVELINES, Versailles (FR)

( * ) Notice: Subject to any disclaimer, the term of this patent is extended or adjusted under 35 U.S.C. 154(b) by 0 days.

(21) Appl. No.: 18/626,942

(22) Filed: Apr. 4, 2024

(30) Foreign Application Priority Data

Feb. 13, 2024 (EP) .................................. 24305248

(51) Int. Cl.
*G16H 50/00* (2018.01)
*G06N 5/022* (2023.01)
(Continued)

(52) U.S. Cl.
CPC ............. *G16H 50/30* (2018.01); *G06N 5/022* (2013.01); *G06N 20/00* (2019.01); *G16B 20/00* (2019.02)

(58) Field of Classification Search
CPC ........ G16H 50/30; G16N 20/00; G16B 20/00; G06N 5/022
See application file for complete search history.

(56) References Cited

U.S. PATENT DOCUMENTS 10,236,078 B2 * 3/2019 Kennedy .......... G01N 33/57407
2010/0329535 A1 * 12/2010 Macenko .................. G06T 7/90
382/133

(Continued)

FOREIGN PATENT DOCUMENTS

EP 4239647 A1 * 9/2023 ............ G06N 3/0454

OTHER PUBLICATIONS

Garberis et al., "Deep Learning Allows Assessment of Risk of Metastatic Relapse from Invasive Breast Cancer Histological Slides", bioRxiv preprint doi: https://doi.org/10.1101/2022.11.28.51815, Dec. 5, 2022, 25 pages.

(Continued)

*Primary Examiner* — Khai M Nguyen

(74) *Attorney, Agent, or Firm* — Maier & Maier, PLLC

(57) ABSTRACT

A method and a device for training a prediction model configured to predict a risk of relapse of a patient afflicted with cancer from a whole histological slide image including (Continued)

a representation of at least one portion of a cancerous tissue of the subject and a method and a device for predicting a risk of relapse of the patient afflicted with cancer using said trained prediction model. Further, a device for predicting a response to cancer treatment of the patient using the trained prediction model.

18 Claims, 4 Drawing Sheets

(51) Int. Cl.
  *G06N 20/00* (2019.01)
  *G16B 20/00* (2019.01)
  *G16H 50/30* (2018.01)

(56) References Cited

U.S. PATENT DOCUMENTS

| | | | | |
|---|---|---|---|---|
| 2019/0015393 | A1* | 1/2019 | Puel | A61K 31/428 |
| 2020/0005901 | A1* | 1/2020 | Cohen | G06N 20/20 |
| 2021/0142904 | A1* | 5/2021 | Michuda | G16H 50/20 |
| 2021/0155982 | A1* | 5/2021 | Yin | G06T 7/136 |
| 2021/0271847 | A1 | 9/2021 | Courtiol et al. | |
| 2022/0292674 | A1* | 9/2022 | Braman | G06T 7/0012 |
| 2023/0250484 | A1* | 8/2023 | Perou | C12Q 1/6886 702/19 |
| 2023/0282362 | A1* | 9/2023 | Saillard | G16H 50/30 702/19 |
| 2024/0006080 | A1* | 1/2024 | Molero Leon | G16B 20/40 |

OTHER PUBLICATIONS

Saillard et al., Self-supervised learning improves dMMR/MSI detection from histology slides across multiple cancers, arXiv:2109.05819v1 [eess.IV], Sep. 13, 2021, 16 pages.

Saillard et al., "PACpAInt: a deep learning approach to identify molecular subtypes of pancreatic adenocarcinoma on histology slides", bioRxiv preprint doi: https://doi.org/10.1101/2022.01.04.474951, Jan. 5, 2022, 17 pages.

Amgad et al., "A Population-Level Digital Histologic Biomarker for Enhanced Prognosis of Invasive Breast Cancer", Nature Medicine, The Author(s), under exclusive licence to Springer Nature America, Inc., Nov. 27, 2023, vol. 30, No. 1, 19 pages.

Diao et al., "Human-Interpretable Image Features Derived from Densely Mapped Cancer Pathology Slides Predict Diverse Molecular Phenotypes", Nature Communications, The Author(s), Mar. 12, 2021, vol. 12, No. 1, 15 pages.

Fernandez et al., "Development and Validation of an AI-Enabled Digital Breast Cancer Assay to Predict Early-Stage Breast Cancer Recurrence Within 6 Years", Breast Cancer Research, The Author(s), Dec. 20, 2022, vol. 24, No. 93, 11 pages.

\* cited by examiner

DEVICE AND METHOD FOR PREDICTING A RELAPSE OF A CANCER FOR A PATIENT

FIELD

The present invention relates to cancer medical technology, in particular the invention relates to a device and associated method for training a prediction model configured to predict a relapse of a patient afflicted with cancer. Furthermore, the invention relates to a device and associated method for predicting a risk of relapse of the patient afflicted with cancer using the trained prediction model, and a device for predicting a response to cancer treatment of the patient using the trained prediction model.

BACKGROUND

Early detection of cancer metastatic relapse lies in its potential to improve patient outcomes, enhance quality of life, and guide the implementation of personalized and effective treatment strategies. It provides a window of opportunity for healthcare professionals to intervene proactively and positively impact the course of cancer. In particular, for a patient afflicted with breast cancer (BC), prediction of metastatic relapse is crucial to provide the patient with the most appropriate treatment in terms of choice of medication as well as dosage. Indeed, the choice of treatment profoundly influences a patient's health status, dictating the trajectory of his recovery or disease management. Well-informed treatment decisions, tailored to the individual's medical profile, can optimize therapeutic efficacy, minimize side effects, and contribute significantly to the overall improvement of the patient's health.

Breast cancer is the most common type of cancer. Approximately 70% of breast cancers are hormone-sensitive (i.e. HR+/HER2−). In particular, 20% of these cancers induce metastatic relapse which greatly reduces patient survivability. Therefore, there is a need for a tool that can predict accurately the risk of relapse of a patient afflicted with cancer which can be used, for instance, to adapt the treatment and follow-up strategies for the patient.

The invention falls within this context.

SUMMARY

This invention thus relates to a device for training a prediction model configured to predict a risk of relapse of a patient afflicted with cancer, wherein the device for training a prediction model comprises:
- at least one input configured to receive a set of data from a plurality of subjects, each subject of said plurality of subjects having received a previous diagnosis for said cancer, wherein said set of data for each subject comprises:
  - at least one whole histological slide image, said image comprising a representation of at least one portion of a cancerous tissue of said subject;
  - clinical information associated to the subject, said clinical information comprising at least a subject health status evaluated subsequently to said previous diagnosis of said cancer;
- at least one processor configured to:
  - define a training dataset comprising a plurality of training samples by, for each subject of the plurality of subjects:
    - detecting cells in the at least one whole histological slide image of said subject and associating each detected cell to a cell class representative of a cell status;
    - segmenting tissues in the at least one whole histological slide image of said subject and associating each segmented tissue to a tissue class representative of a tissue status;
    - for each cell class, extracting at least one cell feature based on the cells detected for said cell class in the at least one whole histological slide image of said subject;
    - for each tissue class, extracting at least one tissue feature based on the portion of the at least one whole histological slide image of said subject relating to the segmented tissue associated to said tissue class;
    - defining one training sample as comprising said at least one cell feature, said at least one tissue feature and said subject health status associated to the subject;
  - train a prediction model using said defined training dataset, wherein the prediction model is configured to receive as input at least one cell feature and at least one tissue feature for a patient, said at least one cell feature and at least one tissue feature being extracted from at least one whole histological slide image said image comprising a representation of at least one portion of a cancerous tissue of said patient and providing as output a risk score representative of a probability of relapse of said patient or representative of the health status of the patient;
- at least one output configured to provide said trained prediction model.

The health status of the subject may be used as a ground truth data during the training.

Advantageously, the present device for training relies on an approach to leveraging histological slide images and clinical data to accurately predict the risk of relapse of the patient afflicted with cancer. By defining the training dataset comprising a plurality of training samples, as described above, the device can extract meaningful tissue and cell features from whole histological slide images. Indeed, cell and tissue features are intrinsically indicative of cancer progression and metastasis, thus informing about a risk of relapse of the patient afflicted with cancer. Through the training of a prediction model on a comprehensive training dataset comprising these features labeled with the subject health status, the device enables healthcare professionals to proactively assess the risk of relapse for patients afflicted with cancer. This approach implemented by the present device for training prompts personalized treatments and effective treatment strategies. Furthermore, by providing a risk score representative of a probability of relapse of the patient or representative of the health status of the patient, the device for training equips healthcare professionals with insights to guide treatment decisions and interventions, thereby positively impacting the overall management of patients afflicted with cancer. According to other advantageous aspects of the invention, the device for training a prediction model comprises one or more of the features described in the following embodiments, taken alone or in any possible combination.

According to one embodiment, the prediction model is a Cox model. Advantageously, a Cox model is adapted to analyze survival data and identify factors that influence the timing of events, such as the risk of relapse of the patient afflicted with cancer or even death.

According to one embodiment, the prediction model is trained using a 5-fold cross-validation scheme. Advantageously, a 5-fold cross-validation scheme ensures the robustness and the generalizability capacities of the prediction model.

According to one embodiment, detecting cells in a whole histological slide image and associating each detected cell to a cell class is performed by a convolutional neural network.

According to one embodiment, segmenting tissues in a whole histological slide image and associating each segmented tissue to a tissue class is performed by a convolutional neural network configured to class each pixel of the whole histological slide image into one tissue class among a plurality of predefined tissue classes. Advantageously, using a convolutional neural network configured to class each pixel of the whole histological slide image is transformative in its ability to automate and standardize the process, enabling precise delineation of tissue regions and facilitating subsequent analysis and tissue features extraction for tasks such as predicting a risk of relapse of a patient afflicted with cancer.

According to one embodiment, extracting at least one tissue feature comprises:
- for each tissue class, identifying nests, being two contiguous segmented tissues portions within the whole slide image, each of said two segmented tissues portions being associated with said tissue class;
- extracting at least one tissue feature based on the identified nests in the whole slide image, and/or
- for each identified nest, extracting at least one tissue feature being a morphological feature.

A nest may be defined as a contiguous set of pixels that are classified to the same class. For example, it is possible to take all pixels predicted as tumors and reducing this pixel map into the set of maximal regions (i.e., nests) where each nest is either 1 pixel, or several pixels where all pixels are adjacent to at least one other tumor pixel. For each nest, no adjacent pixel of any pixel of the nest is of the same class as the class of the nest (i.e., the maximal contiguous regions of pixels of the same class). Advantageously, using nests for extracting a tissue feature allows for the extraction of a tissue feature that captures the spatial relationship and morphological feature unique to a specific tissue class.

According to one embodiment, extracting at least one cell feature comprises:
- for each tissue class, selecting cells comprised in the associated segmented tissues;
- for each cell class, for each selected cell associated to said cell class, computing at least one feature being a morphological feature; and/or
- for a group of cells associated to a same cell class and selected for a same tissue class, extract at least one feature being a statistical feature computed using said group of cells.

Advantageously, extracting at least one cell feature as described above ensures that cell features are extracted within a relevant tissue context. This contextualization allows capturing the heterogeneity of cell classes across different tissue classes, allowing for the extraction of tissue-specific cell features. Moreover, computing morphological features offers information about cellular architecture and organization, which may be indicative of pathological changes or disease progression, such as the relapse of a patient afflicted with cancer. Additionally, by extracting statistical features using the group of cells, collective features of cell classes within a specific tissue class can be captured. These statistical features provide a quantitative representation of cellular behavior and spatial organization within tissues.

According to one embodiment, the cancer is a breast cancer. The breast cancer may be a HR$^+$/HER2$^-$ breast cancer (hormone receptor-positive (HR$^+$) and HER2– negative (HER2$^-$) breast cancer with HER2 standing for human epidermal growth factor receptor 2), in particular early invasive HR$^+$/HER2$^-$ breast cancer. The breast cancer may be a HR$^+$/HER2$^-$ breast cancer wherein the patient/subject has stage 2 or stage 3 cancer (i.e., not stage 0, nor stage 1, nor stage 4). These characteristics characterize a first group of patients for which the methods of the present invention may be advantageously used. The breast cancer may be a HR$^+$/HER2$^-$ breast cancer wherein the patient/subject also has at least 4 positive lymph nodes; or between 1 and 3 positive lymph nodes and one of grade 3 tumor, or tumor size equal or superior to 50 mm, or Ki67 equal or superior to 20%. These characteristics characterizes a second group of patients for which the methods of the present invention may be advantageously used.

According to one embodiment, where the cancer is a breast cancer, the clinical information associated to one subject is comprised in the training sample, the prediction model is configured to receive as input at least one clinical information associated to the subject 22 and the clinical information further comprises at least one of the following: tumor size, menopausal status, grade of the tumor, progesterone receptor positivity, Ki67 protein estimation as a percentage, number of positive lymph nodes, the presence of micrometastases only in lymph nodes, age at diagnosis, percentage of cells positive to the progesterone receptor, intensity of the progesterone receptor, estrogen receptor positivity, percentage of cells positive to the estrogen receptor, intensity of the estrogen receptor, human epidermal growth factor receptor 2 positivity, percentage of cells positive to the human epidermal growth factor receptor 2, intensity of the human epidermal growth factor receptor 2, the mutational status of BRCA1, the mutational status of BRCA2, type of surgery, residual tumor classification, histology tumor type, pathological T stage, pathological N stage, pathological M stage, type of treatments received and duration of treatments received.

The present invention further relates to a device for predicting a risk of relapse of a patient afflicted with cancer using a trained prediction model obtained from the device according to any one of the previous embodiments, said device for predicting a risk of relapse comprising:
- at least one input configured to receive at least one whole histological slide image said image comprising a representation of at least one portion of a cancerous tissue of said patient;
- at least one processor configured to:
  - detect cells in the at least one whole histological slide image of said patient and associate each detected cell to a cell class representative of a cell status;
  - segment tissues in the at least one whole histological slide image of said patient and associate each segmented tissue to a tissue class representative of a tissue status;
  - for each cell class, extract at least one cell feature based on the cells detected for said cell class in the at least one whole histological slide image of said patient;
  - for each tissue class, extract at least one tissue feature based on the portion of the at least one whole histological slide image of said patient relating to the segmented tissue associated to said tissue class;

provide as input to said trained prediction model said at least one cell feature and at least one tissue feature, obtaining a risk score representative of a probability of relapse of said patient or representative of the health status of the patient;

at least one output configured to provide said risk score.

The present invention also pertains to a computer-implemented method for training a prediction model to predict a relapse of a patient afflicted with cancer, said method for training a prediction model comprising:

receiving a set of data from a plurality of subjects, each subject of said plurality of subjects having received a previous diagnosis for said cancer, wherein said set of data for each subject comprises:
  at least one whole histological slide image, said image comprising a representation of at least one portion of a cancerous tissue of said subject;
  clinical information associated to the subject, said clinical information comprising at least a subject health status evaluated subsequently to said previous diagnosis of said cancer;

defining a training dataset comprising a plurality of training samples by, for each subject of the plurality of subjects:
  detecting cells in the at least one whole histological slide image of said subject and associating each detected cell to a cell class representative of a cell status;
  segmenting tissues in the at least one whole histological slide image of said subject and associating each segmented tissue to a tissue class representative of a tissue status;
  for each cell class, extracting at least one cell feature based on the cells detected for said cell class in the at least one whole histological slide image of said subject;
  for each tissue class, extracting at least one tissue feature based on the portion of the at least one whole histological slide image of said subject relating to the segmented tissue associated to said tissue class;
  defining one training sample as comprising said at least one cell feature, said at least one tissue feature and said subject health status associated to the subject;

training a prediction model using said defined training dataset, wherein the prediction model is configured to receive as input at least one cell feature and at least one tissue feature for a patient, said at least one cell feature and at least one tissue feature being extracted from at least one whole histological slide image said image comprising a representation of at least one portion of a cancerous tissue of said patient and providing as output a risk score representative of a probability of relapse of said patient or representative of the health status of the patient;

outputting said trained prediction model.

The present invention also pertains to a computer-implemented method for predicting a risk of relapse of a patient afflicted with cancer using a trained prediction model obtained from the method according to any one of the previous embodiments, said method for predicting a risk of relapse comprising:

receiving at least one whole histological slide image said image comprising a representation of at least one portion of a cancerous tissue of said patient;

detecting cells in the at least one whole histological slide image of said patient and associate each detected cell to a cell class representative of a cell status;

segmenting tissues in the at least one whole histological slide image of said patient and associate each segmented tissue to a tissue class representative of a tissue status;

for each cell class, extracting at least one cell feature based on the cells detected for said cell class in the at least one whole histological slide image of said patient;

for each tissue class, extracting at least one tissue feature based on the portion of the at least one whole histological slide image of said patient relating to the segmented tissue associated to said tissue class;

providing as input to said trained prediction model said at least one cell feature and said at least one tissue feature, obtaining a risk score representative of a probability of relapse of said patient or representative of the health status of the patient;

outputting said risk score.

The present invention also pertains to a device for predicting a response to cancer treatment of a patient using a trained prediction model obtained from the device according to any one of the embodiments hereabove, said device for predicting a response to cancer treatment comprising:

at least one input configured to receive at least one whole histological slide image of said patient;

at least one processor configured to:
  detect cells in the at least one whole histological slide image of said patient and associating each detected cell to a cell class representative of a cell status;
  segment tissues in the at least one whole histological slide image of said patient and associating each segmented tissue to a tissue class representative of a tissue status;
  for each cell class, extract at least one cell feature based on the cells detected for said cell class in the at least one whole histological slide image of said patient;
  for each tissue class, extract at least one tissue feature based on the portion of the at least one whole histological slide image of said patient relating to the segmented tissue associated to said tissue class;
  provide as input to said trained prediction model said at least one cell feature and at least one tissue feature, obtaining a risk score representative of a probability of relapse of said patient or representative of the health status of the patient;
  use said risk score for predicting a response to cancer treatment of the patient;

at least one output configured to provide said response to cancer treatment of the patient.

The present invention further relates to a method for predicting the risk of relapse of a patient afflicted with cancer, said method comprising analyzing at least one whole histological slide image 23 comprising a representation of at least one portion of a cancerous tissue of the patient.

According to one embodiment, in the method for predicting the risk of relapse of a patient afflicted with cancer, said cancer is breast cancer.

According to one embodiment, said breast cancer is HR+/HER2− breast cancer, in particular early invasive HR+/HER2− breast cancer.

According to one embodiment, analyzing at least one whole histological slide image 23 of the patient comprises, using at least one processor:

detecting cells in said at least one whole histological slide image 23 and associating each detected cell to a cell class representative of a cell status;

segmenting tissues in said at least one whole histological slide image 23 and associating each segmented tissue to a tissue class representative of a tissue status;

for each cell class, extracting at least one cell feature based on the cells detected for said cell class in the at least one whole histological slide image 23;

for each tissue class, extracting at least one tissue feature based on the portion of the at least one whole histological slide image 23 relating to the segmented tissue associated to said tissue class;

using said at least one cell feature and at least one tissue feature to predict the risk of relapse of a patient afflicted with cancer.

The present invention further relates to a method for treating cancer in a patient depending on their risk of relapse, said method comprising:

determining whether the patient suffering from cancer is at low risk of relapse or not at low risk of relapse (for example at high risk of relapse) using a method according to any of the previous embodiments; and implementing an adapted patient care depending on the risk of relapse, said adapted patient care comprising surgery, radiotherapy, hormone therapy, chemotherapy, and/or an anti-relapse drug (such as a cyclin-dependent kinase 4 and/or 6 inhibitor (CDK4/6i)).

According to one embodiment, the patient is determined to be at low risk of relapse and the adapted patient care comprises surgery, radiotherapy, hormone therapy and/or chemotherapy.

According to one embodiment, the patient is determined to be not at low risk of relapse (for example at high risk of relapse) and the adapted patient care comprises:

surgery, radiotherapy, hormone therapy and/or chemotherapy, and an anti-relapse drug such as a cyclin-dependent kinase 4 and/or 6 inhibitor (CDK4/6i).

In addition, the disclosure relates to a computer program comprising software code adapted to perform a method for predicting or a method for training compliant with any of the above execution modes when the program is executed by a processor.

The present disclosure further pertains to a non-transitory program storage device, readable by a computer, tangibly embodying a program of instructions executable by the computer to perform a method for predicting or a method for training, compliant with the present disclosure.

Such a non-transitory program storage device can be, without limitation, an electronic, magnetic, optical, electromagnetic, infrared, or semiconductor device, or any suitable combination of the foregoing. It is to be appreciated that the following, while providing more specific examples, is merely an illustrative and not exhaustive listing as readily appreciated by one of ordinary skill in the art: a portable computer diskette, a hard disk, a ROM, an EPROM (Erasable Programmable ROM) or a Flash memory, a portable CD-ROM (Compact-Disc ROM).

DEFINITIONS

In the present invention, the following terms have the following meanings:

The terms "a" and "an" refer to one or to more than one (i.e., to at least one) of the grammatical object of the article. By way of example, "an element" means one element or more than one element. Similarly, the expressions "at least one" and "one or more" are interchangeable.

The terms "adapted" and "configured" are used in the present disclosure as broadly encompassing initial configuration, later adaptation or complementation of the present device, or any combination thereof alike, whether effected through material or software means (including firmware).

The term "processor" should not be construed to be restricted to hardware capable of executing software, and refers in a general way to a processing device, which can for example include a computer, a microprocessor, an integrated circuit, or a programmable logic device (PLD). The processor may also encompass one or more Graphics Processing Units (GPU), whether exploited for computer graphics and image processing or other functions. Additionally, the instructions and/or data enabling to perform associated and/or resulting functionalities may be stored on any processor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

"Machine learning (ML)" designates in a traditional way computer algorithms improving automatically through experience, on the ground of training data enabling to adjust parameters of computer models through gap reductions between expected outputs extracted from the training data and evaluated outputs computed by the computer models.

A "hyper-parameter" presently means a parameter used to carry out an upstream control of a model construction, such as a remembering-forgetting balance in sample selection or a width of a time window, by contrast with a parameter of a model itself, which depends on specific situations. In ML applications, hyper-parameters are used to control the learning process.

"Datasets" are collections of data used to build an ML mathematical model, so as to make data-driven predictions or decisions. In "supervised learning" (i.e. inferring functions from known input-output examples in the form of labelled training data), three types of ML datasets (also designated as ML sets) are typically dedicated to three respective kinds of tasks: "training", i.e. fitting the parameters, "validation", i.e. tuning ML hyperparameters (which are parameters used to control the learning process), and "testing", i.e. checking independently of a training/validation dataset exploited for building a mathematical model that the latter model provides satisfying results. In "unsupervised learning", hyper-parameters may control factors such as cluster assignment criteria or convergence thresholds. For example, in clustering algorithms like k-means, the number of clusters is a hyper-parameter that influences the model's behavior. Similarly, in dimensionality reduction techniques like principal component analysis (PCA), the number of principal components retained can be considered a hyperparameter affecting the resulting representation of the data. Additionally, "unsupervised learning" datasets lack explicit labels or annotations, and instead consist of raw data points or features. In "unsupervised learning" tasks, the entire dataset is typically used for training, as there are no predefined target outputs. The absence of labels in unsupervised datasets necessitates alternative methods for evaluating model performance, such as assessing the coherence of clusters or the preservation of data structure in the reduced-dimensional space.

A "neural network (NN)" designates a category of ML comprising nodes (called "neurons"), and connections between neurons modeled by "weights". For each neuron, an output is given in function of an input or a set of inputs by an "activation function". Neurons are generally organized into multiple "layers", so that neurons of one layer connect only to neurons of the immediately preceding and immediately following layers. In the context of Residual Neural Networks (RNNs), "residual connections" can be used to facilitate more efficient gradient propagation across multiple time steps. A "residual connection" is a shortcut connection in a "neural network" architecture where the input of a certain layer is added to the output of a subsequent layer. Such "residual connections" enhance the network's ability to capture long-range dependencies and temporal patterns in sequential data. "Residual connections" allow to counteract the challenge of vanishing or exploding gradients during training.

The above ML definitions are compliant with their usual meaning, and can be completed with numerous associated features and properties, and definitions of related numerical objects, well known to a person skilled in the ML field. Additional terms will be defined, specified or commented wherever useful throughout the following description.

BRIEF DESCRIPTION OF THE DRAWINGS

The present disclosure will be better understood, and other specific features and advantages will emerge upon reading the following description of particular and non-restrictive illustrative embodiments, the description making reference to the annexed drawings wherein.

On the figures, the drawings are not to scale, and identical or similar elements are designated by the same references.

DETAILED DESCRIPTION

The present description illustrates the principles of the present disclosure. It will thus be appreciated that those skilled in the art will be able to devise various arrangements that, although not explicitly described or shown herein, embody the principles of the disclosure and are included within its scope.

All examples and conditional language recited herein are intended for educational purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein may represent conceptual views of illustrative circuitry embodying the principles of the disclosure. Similarly, it will be appreciated that any flow charts, flow diagrams, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, a single shared processor, or a plurality of individual processors, some of which may be shared.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

Figure 1:
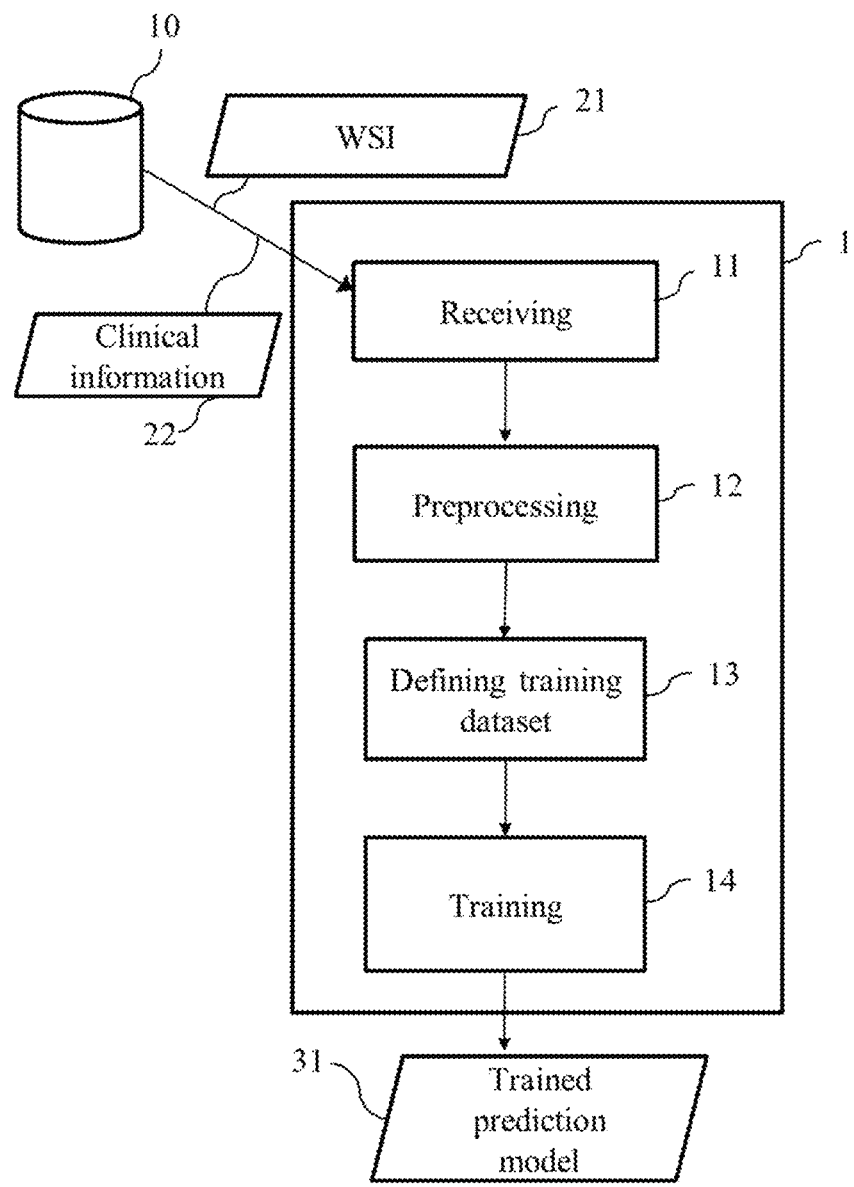
FIG. 1 is a block diagram representing schematically a particular mode of a device for training a prediction model configured to predict a relapse of a patient afflicted with cancer, compliant with the present disclosure.

The present disclosure will be described in reference to a particular functional embodiment of a device 1 for training a prediction model configured to predict a relapse of a patient afflicted with cancer, as illustrated on FIG. 1.

The device 1 is adapted to receive at least one input configured to receive a set of data from a plurality of subjects having received a previous diagnosis for said cancer to be used to define a labeled training dataset.

Furthermore, the device 1 is configured to output a trained prediction model 31 configured to provide a risk score allowing to evaluate a probability/risk of a relapse of a patient afflicted with cancer.

The device 1 is associated with a device 6 for using the trained prediction model 31, wherein device 6 is configured to receive as input at least one whole histological slide image 23 comprising a representation of at least one portion of a cancerous tissue of the patient, and to output a risk score representative of a probability of relapse of said patient or representative of the health status of the patient. Device 6 is represented on FIG. 3 and will be subsequently described.

Though the presently described devices 1 and 6 are versatile and provided with several functions that can be carried out alternatively or in any cumulative way, other implementations within the scope of the present disclosure include devices having only parts of the present functionalities.

Each of the devices 1 and 6 are advantageously an apparatus, or a physical part of an apparatus, designed, configured and/or adapted for performing the mentioned functions and produce the mentioned effects or results. In alternative implementations, the device 1 and the device 6 is embodied as a set of apparatus or physical parts of apparatus, whether grouped in a same machine or in different, possibly remote, machines. The device 1 and/or the device 6 may e.g. have functions distributed over a cloud infrastructure and be available to users as a cloud-based service or have remote functions accessible through an API.

The device 1 and the device 6 may be integrated in a same apparatus or set of apparatus, and intended to same users. In other implementations, the structure of device 6 may be completely independent of the structure of device 1, and may be provided for other users.

In what follows, the modules are to be understood as functional entities rather than material, physically distinct, components. They can consequently be embodied either as grouped together in a same tangible and concrete component, or distributed into several such components. Also, each of those modules is possibly itself shared between at least two physical components. In addition, the modules are implemented in hardware, software, firmware, or any mixed form thereof as well. They are preferably embodied within at least one processor of the device 1 or of the device 6.

The device 1 comprises a module 11 for receiving a set of data from a plurality of subjects, each subject having received a previous diagnosis for a cancer, wherein the set of data for each subject comprises at least one whole histological slide image 21 of the subject and clinical information associated to the subject 22, the clinical information comprising at least a subject health status evaluated subsequently to the previous diagnosis of the cancer. The set of data from a plurality of subjects may be stored in one or more local or remote database(s) 10. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk).

In one or several embodiments, the set of data from a plurality of subjects consists of a set of data from a group of subjects with non-metastatic cancer, in particular non-metastatic breast cancer. In one or several embodiments, the set of data from a plurality of subjects consists of a set of data from a group of subjects with non-metastatic $HR^+/HER2^-$ breast cancer.

As used herein, whole histological slide image means an image of a tissue section obtained with whole slide imaging. Typically, to perform histological analysis by microscopic examination, a prepared tissue section is transferred to a glass slide and stained, for example with HE (hematoxylin and eosin) or HES (hematoxylin, eosin, and safranin). The resulting glass slide is usually referred to as a histological slide or a tissue slide. Typically, the preparation of a tissue section for histological analyses may include fixation of the tissue, trimming of the tissue, dehydration of the tissue, and embedding of the tissue in paraffin wax prior to section with a microtome. Whole slide imaging allows to digitally scan and archive a whole histological slide in high resolution. During scanning, images are taken of each field of view across the entire histological slide and simultaneously stitched together to create a single digital image, which is referred herein as a whole histological slide image.

The whole histological slide image 21 may correspond to an image of a section of tissue previously extracted from the subject's breast. For example, the tissue may have been extracted by surgery or biopsy. As indicated above, the whole histological slide may have been stained with HE (Hematoxylin and Eosin) or HES (Hematoxylin, Eosin, and Safranin).

The clinical information comprises at least a subject health status (e.g. survival data) evaluated subsequently to the previous diagnosis of the cancer. The subject health status may comprise at least one evaluation of the subject health status and an associated time information, such as the date of said evaluation or the time period passed from the first diagnosis. The subject health status may have been evaluated at predefined time steps, for instance, on a monthly basis (e.g. every 6 months). The subject health status refers to death or relapse events or disease progression events. For example, the subject health status can include follow-up data such as a date of diagnosis, a date of last follow-up without any relapse events, a death date. The subject health status could include follow-up data such as a type of relapse: distant relapse, local relapse, regional relapse or metastatic relapse.

In one example, the subject health status entails two variables: the first variable is a binary value indicating whether the patient has had an event (e.g. patient died, so the binary value=1) and the second variable is the time of the event since the date of surgery (i.e. 2 years, to indicate that the patient died 2 years after undergoing a surgery for treating the cancer). In another example, the first variable (binary value) can indicate that the patient did not have an event (i.e. patient did not die, so the binary value=0), and the second variable is the time of the last follow-up (time when the health status of the patient is assessed) since the date of surgery.

The time of the event may be evaluated relatively to the date of diagnosis, the date of biopsy, the date of treatment initiation, the date or surgery, or any other relevant date.

In one or several embodiments, the clinical information associated to the subject 22 (in brief, the clinical information) may include clinical variables such as age, sex, menopausal status, grade of the tumor, histological type of cancer, Ki67 protein estimation, progesterone receptor positivity, the percentage of estrogen and progesterone extracted from immunohistochemistry slides, the number of positive lymph nodes, and/or tumor size.

The clinical information associated to the subject 22 (in brief, the clinical information) may include clinical variables such as tumor size, menopausal status, grade of the tumor, progesterone receptor positivity, Ki67 protein estimation as a percentage, number of positive lymph nodes, the presence of micrometastases only in lymph nodes, age at diagnosis, percentage of cells positive to the progesterone receptor, intensity of the progesterone receptor, estrogen receptor positivity, percentage of cells positive to the estrogen receptor, intensity of the estrogen receptor, human epidermal growth factor receptor 2 positivity, percentage of cells positive to the human epidermal growth factor receptor 2, intensity of the human epidermal growth factor receptor 2, the mutational status of BRCA1, the mutational status of BRCA2, type of surgery, residual tumor classification, histology tumor type, pathological T stage, pathological N stage, pathological M stage, and/or type of treatments received and duration of treatments received.

For example, the clinical information may have been collected/computed by a health professional (e.g. pathologist, radiologist, geneticist).

The device 1 further comprises optionally a module 12 for preprocessing the received set of data from a plurality of subjects. The module 12 may notably be adapted to standardize the whole histological slide image 21 for sake of efficient and reliable processing. It may transform the image data 21, i.e. by image filtering or by pixels values normalization. It may also extract features from whole histological slide image 21. According to various configurations, the module 12 is adapted to execute only part or all of the above functions, in any possible combination, in any manner suited to the following processing stage.

The device 1 may further comprise a module 13 for defining a training dataset comprising a plurality of training samples from a set of data from the plurality of subjects. Module 13 may be configured to, for each subject, analyze the whole histological slide image 21 focusing in one phase on the cells and in the other phase on the tissues comprised in said image 21.

Notably, module 13 may be configured to execute a first phase comprising, for each subject: (1) detecting cells in the at least one whole histological slide image 21 of the subject and associating each detected cell to a cell class representative of a cell status (i.e., cells annotation) and (2) for each tissue class, extracting at least one tissue feature based on the portion of the at least one whole histological slide image 21 of said subject relating to the segmented tissue associated to said tissue class.

The cell class representative of the cell status may be a class indicating that a cell is cancerous or non-cancerous. A non-cancerous cell could be a connective cell, an inflammatory cell, or a normal epithelial cell. For instance, cells could be assigned to one of four classes: tumor cell, connective cell, inflammatory cell, or normal epithelial cell.

Cells annotation may be achieved using other machine learning models or manually. A convolutional neural network (e.g., U-Net, Res-Net or RNN) may be used to detect cells in the whole histological slide image and associate each detected cell to a cell class.

In one or several embodiments, cells annotation can be achieved through the implementation by module 13 of a One-Stage Object Detection (FCOS) model. For example, the FCOS model may be trained using manually curated ground-truth annotations from patches of whole histological slide images acquired at a cell zoom ratio. In one example, a ResNet50 architecture can be used as the backbone model.

The module 13 may be configured to execute a second phase, now focusing on the tissues, comprising, for each subject of the plurality of subject: (1) segmenting tissues in the at least one whole histological slide image 21 of said subject and associating each segmented tissue to a tissue class representative of a tissue status (i.e., tissues annotation); for each tissue class, extracting at least one tissue feature based on the portion of the at least one whole histological slide image 21 of said subject relating to the segmented tissue associated to said tissue class. It is to be noted that these first and second phases may be implemented no matter the other or simultaneously.

The tissue class representative of the tissue status may be a class indicating that a tissue is cancerous or non-cancerous. A non-cancerous tissue could be a benign gland, a necrotic tissue, an inflammatory tissue, or other non-cancerous tissue. For instance, tissues could be assigned to one of seven classes: tumorous tissue, tumor stroma, inflammatory tissue, in-situ tumor, benign glad, necrotic tissue or other non-cancerous tissue.

Segmenting tissues in a whole histological slide image and associating each segmented tissue to a tissue class may be performed by a convolutional neural network (e.g., Res-U-Net, Seg-Net, FCN) configured to class each pixel of the whole histological slide image into one tissue class among a plurality of predefined tissue classes.

In one or several embodiments, tissues annotation can be achieved, by module 13, using a U-Net model. For example, the U-Net model may be trained using manually curated ground-truth annotations from patches of whole histological slide images acquired at a tissue zoom ratio. In one example, a MobileNet-v3-large architecture can be used as the backbone model.

In alternative embodiments, tissues annotation can be achieved using other machine learning models or manually.

For each whole histological slide image 21, feature values are computed from the obtained cells and tissues annotations.

For each cell class, at least one cell feature based on the cells detected for this specific cell class is extracted. A cell feature may be one of the following:

Cell count: it consists in counting the number of detected cells of the cell class in the complete tissue (i.e. the whole histological slide image without non-tissue areas) and/or in each of the detected tissue classes.

Cell density: it consists in counting the number of detected cells divided by the total number of pixels in the complete tissue (i.e. the whole histological slide image without non-tissue areas) and/or in each of the detected tissue classes.

Paired proportion: it consists in calculating for a pair of cells a ratio of the number of detected cells of a first cell class, associated to a first cell of the pair of cells, divided by the number of detected cells of a second cell class, associated to a second cell of the pair of cells; the ratio is calculated in the complete tissue (i.e. the whole histological slide image without non-tissue areas) and/or in each of the detected tissue classes. In practice, the paired proportion can be calculated as $$\frac{A-B}{A+B}$$

where A is the number of detected cells of the first cell class and B is the number of detected cells of the second cell class, the paired proportion being calculated as such for machine learning stability and solution viability.

Relative proportion: it consists in calculating, for each cell class, the number of detected cells of this class divided by the total number of detected cells in the complete tissue (i.e. the whole histological slide image without non-tissue areas) and/or in each of the detected tissue classes.

For each tissue class, at least one tissue feature is extracted based on the portion of the whole histological slide image relating to the segmented tissue associated to the tissue class. A tissue feature may be one of the following:

Spatiality of tissue regions: it consists in calculating, for each tissue class, a morphological feature such as eccentricity, major axis length, minor axis length, perimeter, area, perimeter divided by area, solidity, convex area, spread or extent.

Spatiality of tissue nests: it consists in calculating, for each tissue class, a group of mathematical descriptors. For each tissue class, contiguous regions within the whole histological slide image are identified and denoted as "nests". Then, a set of features may be extracted, the set containing for example the count of nests, the count of nests over the total segmented pixels of the associated segmented class and/or the count of nests over the total segmented pixels of tissue. After that, for each nest, mathematical descriptors may be computed per morphological feature. Mathematical descriptors may be a mean, a percentile (25%, 50% (i.e. median), 75%), a largest value (i.e. maximum) for the nest with the largest area, a mean of 5 values for the 5 nests with largest area, a mean of 20 values for the 20 nests with largest area.

Size descriptors of cells: it consists in calculating, for each tissue class (i.e. 7 classes from segmentation and the whole tissue) and for each cell class (i.e. 4 classes), descriptors for each cell for example the area, the size of the largest length, the size of the lowest length. Then, computing descriptors from all cells of each cell detection class of each tissue class such as the mean, the standard deviation, the mean of the size of the lowest length over the size of the largest length, the standard deviation of the size of the lowest length over the size of the largest length.

Tissue count: it consists in calculating the total number of pixels of a tissue class.

Tissue density: it consists in calculating the ratio of the total number of pixels of a tissue class divided by the total number of pixels of the complete tissue.

Tissue paired proportion: it consists in calculating for a pair of pixels associated to tissue classes, a ratio of the number of detected pixels of a first tissue class, associated to the first pixel of the pair of pixels, divided by the number of detected pixels of a second tissue class, associated to the second pixel of the pair of pixels; the ratio is calculated in the complete tissue (i.e. the whole histological slide image without non-tissue areas) and/or in each of the detected tissue classes. In practice, the tissue paired proportion can be calculated as $$\frac{C-D}{C+D},$$

where C is the number of detected pixels of the first tissue class and D is the number of detected pixels of the second tissue class, the tissue paired proportion being calculated as such for machine learning stability and solution viability.

Tissue relative proportion: it consists in calculating, for each tissue class, the number of detected pixels of this tissue class divided by the total number of detected pixels in the complete tissue (i.e. the whole histological slide image without non-tissue areas) and/or in each of the detected tissue classes.

Finally, module 13 is configured to define the training dataset by defining one training sample as comprising said at least one cell feature, said at least one tissue feature and said subject health status associated to the subject.

It may be observed that the operations by the modules 11, 12 and 13 are not necessarily successive in time, and may overlap, proceed in parallel or alternate, in any appropriate manner. For example, new image data 21 may be progressively received over time and preprocessed, while the module 13 is dealing with the previously obtained image data. In alternative examples, a batch of image data 21 corresponding to a complete time sequence range may be fully received and preprocessed before it is submitted to the module 13.

The device 1 further comprises a module 14 for training the prediction model of a relapse of the patient afflicted with cancer using the defined training dataset, wherein the prediction model is configured to receive as input at least one cell feature and at least one tissue feature for a patient, the cell feature(s) and the tissue feature(s) being extracted from the whole histological slide image 23 of the patient and providing as output a risk score allowing at least to establish a prediction of a relapse of the patient or to predict future health status of the patient. The risk score may be representative of a probability of relapse of said patient and notably the risk score may be a relative risk score (i.e., relative probability of relapse of said patient) or an absolute risk score (i.e., absolute probability of relapse of said patient).

The architecture of the prediction model that may be trained by module 14 is a Cox model. Alternatively, the prediction model may be chosen from a wide range of models that can be used with this setup including XGBoost, L1-Cox, L2-Cox, or any type of regression model with a survival loss, as well as all classification models for predicting an event at a given timestep (e.g., at 5 years) including logistic regression, XGBoost, neural networks, SVM (Support Vector Machine), random forests and the like.

The prediction model, notably the Cox model, may be trained using a 5-fold cross-validation scheme or a leave-one-out cross-validation scheme.

The prediction model (e.g., Cox model) may be configured to receive as input one or several cell features and one or several tissue features, and to provide as output a risk score (e.g., a probability of relapse of the patient, an absolute risk of relapse ranging from −infinity to +infinity, a rank of risk compared to their risk of developing a relapse).

For example, to train a Cox model, the defined training dataset may be fit to the Cox model. For the training, options such as the type of optimization algorithm (e.g., Newton-Raphson, Broyden-Fletcher-Goldfarb-Shanno algorithm) to use, handling ties in the data (e.g., Breslow method, Efron method, Exact partial likelihood), and specifying penalization if necessary (e.g., L1 or L2 regularization, Elastic Net) are specified. After fitting the Cox model, the model's prediction performance may be evaluated to assess whether the performance meets the assumptions of the Cox model, particularly the proportional hazards assumption. This can involve visual inspection of diagnostic plots (e.g., Kaplan-Meier curves, Schoenfeld residual plots, Martingale residuals) or statistical tests (e.g., Likelihood ratio test, Score logrank test, Schoenfeld test). Finally, the coefficients of the fitted Cox model may be inspected to understand the relationship between the model's prediction (i.e., risk score) and the hazard rate (e.g., relapse event, death event).

In another example, a XGBoost model may be used. In this case, the defined training dataset is fitted to the model. During training, various options are specified, including the choice of optimization algorithm (e.g., gradient boosting), handling missing values, and specifying hyperparameters (e.g., learning rate, tree depth). Additionally, techniques like early stopping and cross-validation may be employed to optimize model performance and prevent overfitting. After fitting the XGBoost model, its prediction performance is evaluated to ensure it meets the assumptions of the model, such as the absence of multicollinearity and adherence to the proportional hazards assumption. This evaluation can involve visual inspection of diagnostic plots (e.g., feature importance plots, learning curves) as well as statistical tests (e.g., Kolmogorov-Smirnov test, Shapiro-Wilk test). Finally, the model's output (i.e., risk score) is analyzed to understand its relationship with the target variable (e.g., relapse event, death event).

Figure 3:
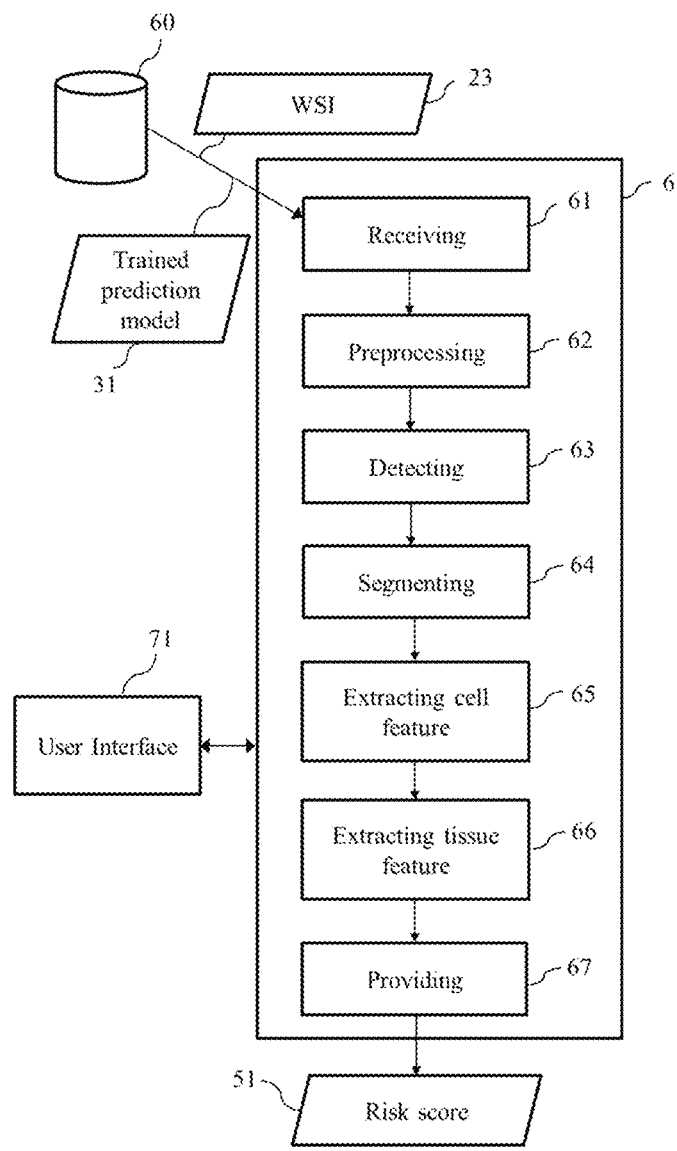
FIG. 3 is a block diagram representing schematically a particular mode of a device for predicting a relapse of a patient afflicted with cancer using a trained prediction model obtained with the device of FIG. 1.

The present disclosure will be further described in reference to a particular functional embodiment of a device 6 configured to receive as input the trained prediction model 31 and at least one whole histological slide image 23 of the patient, and to output a risk score 51 representative of a probability of relapse of said patient or representative of the health status of the patient, as illustrated on FIG. 3.

The device 6 comprises a module 61 for using the trained prediction model 31 (or for receiving as input the training parameters of the trained prediction model 31) and for receiving as input a whole histological slide image 23 stored in one or more local or remote database(s) 60. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk). In one embodiment, the trained prediction model 31 has been previously generated by a system including the device 1 for training. Alternatively, the trained prediction model 31 is received from a communication network.

The device 6 further comprises optionally a module 62 for preprocessing the whole histological slide image 23. The module 62 may notably be adapted to standardize the whole histological slide image 23 for sake of efficient and reliable processing. It may transform the image data 23, i.e. by image filtering or by pixels values normalization. It may also extract features from whole histological slide image 23. According to various configurations, the module 62 is adapted to execute only part or all of the above functions, in any possible combination, in any manner suited to the following processing stage.

The device 6 may further comprise a module 63 for detecting cells in the whole histological slide image 23 of the patient and associating each detected cell to a cell class representative of a cell status (i.e., cells annotation).

The device 6 may further comprise a module 64 for segmenting tissues in the whole histological slide image 23 and associating each segmented tissue to a tissue class representative of a tissue status (i.e., tissues annotation).

The device 6 may further comprise a module 65 for extracting a cell feature based on the cells detected for a cell class in the whole histological slide image 23 of the patient, and that for each cell class.

The device 6 may further comprise a module 66 for extracting a tissue feature based on the portion of the whole histological slide image 23 of the patient relating to the segmented tissue associated to a tissue class, and that for each tissue class.

The modules 63, 64, 65 and 66 of device 6 may be configured to analyze the images and extract the features in a same or similar manner than module 13 of device 1.

The device 6 may further comprise a module 67 for providing as input to the trained prediction model 31 at least one cell feature and at least one tissue feature and obtaining a risk score representative of a probability of relapse of said patient or representative of the health status of the patient.

The device 6 is interacting with a user interface 71, via which information can be entered and retrieved by a user. The user interface 71 includes any means appropriate for entering or retrieving data, information or instructions, notably visual, tactile and/or audio capacities that can encompass any or several of the following means as well known by a person skilled in the art: a screen, a keyboard, a trackball, a touchpad, a touchscreen, a loudspeaker, a voice recognition system.

Figure 2:
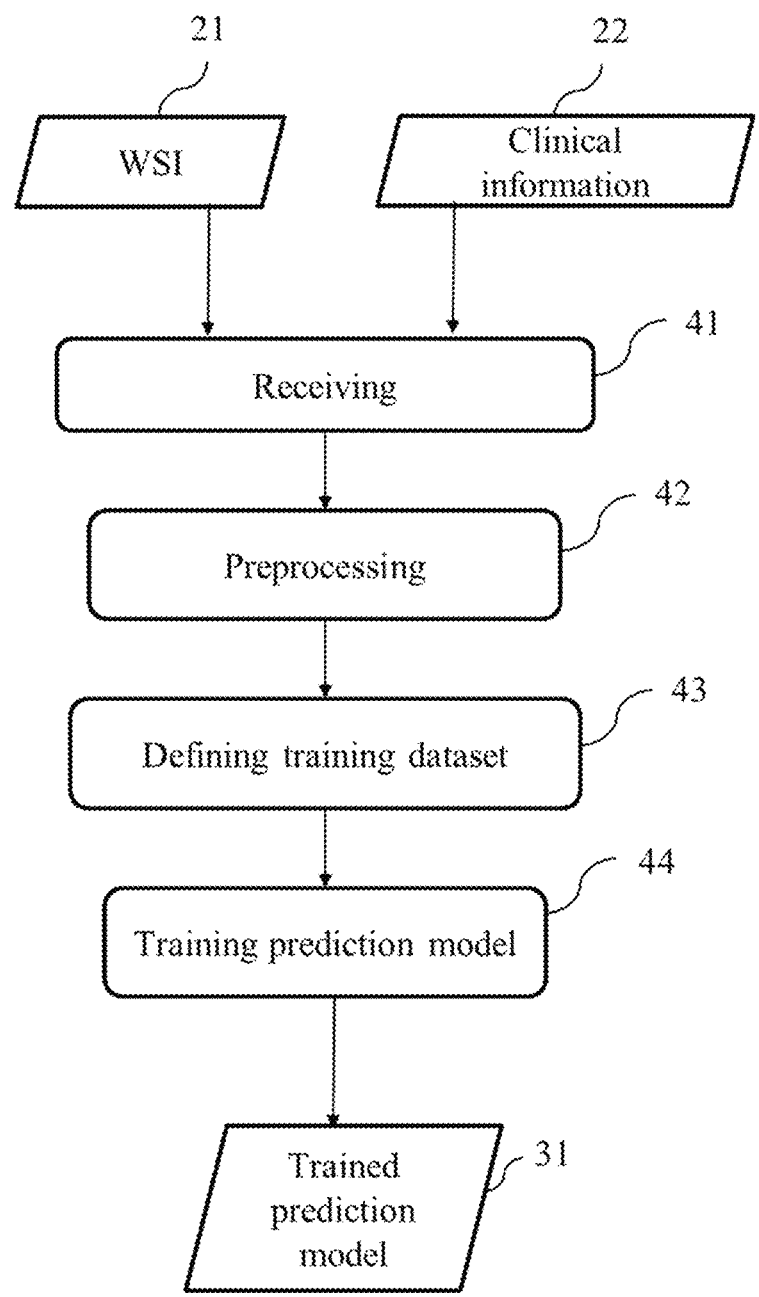
FIG. 2 is a flow chart showing successive steps of a computer-implemented method for training a prediction model to predict a relapse of a patient afflicted with cancer executed with the device of FIG. 1.

In its automatic actions, the device 1 may for example execute the following process (FIG. 2):
receiving a set of data from a plurality of subjects (step 41),
preprocessing the set of data (step 42),
defining a training dataset comprising a plurality of training samples comprising at least one cell feature and at least one tissue feature for each subject (step 43);
training a prediction model using said defined training dataset, wherein the prediction model is configured to receive as input at least one cell feature and at least one tissue feature for a patient, said at least one cell feature and at least one tissue feature being extracted from at least one whole histological slide image 23 said image comprising a representation of at least one portion of a cancerous tissue of said patient and providing as output a prediction of a relapse of said patient (step 44);
outputting said trained prediction model 31.

All of the image processing techniques and features extraction approaches applied on the whole histological image 21 of said subject might also be applied to the whole histological image 23 of said patient in any possible combination.

Figure 4:
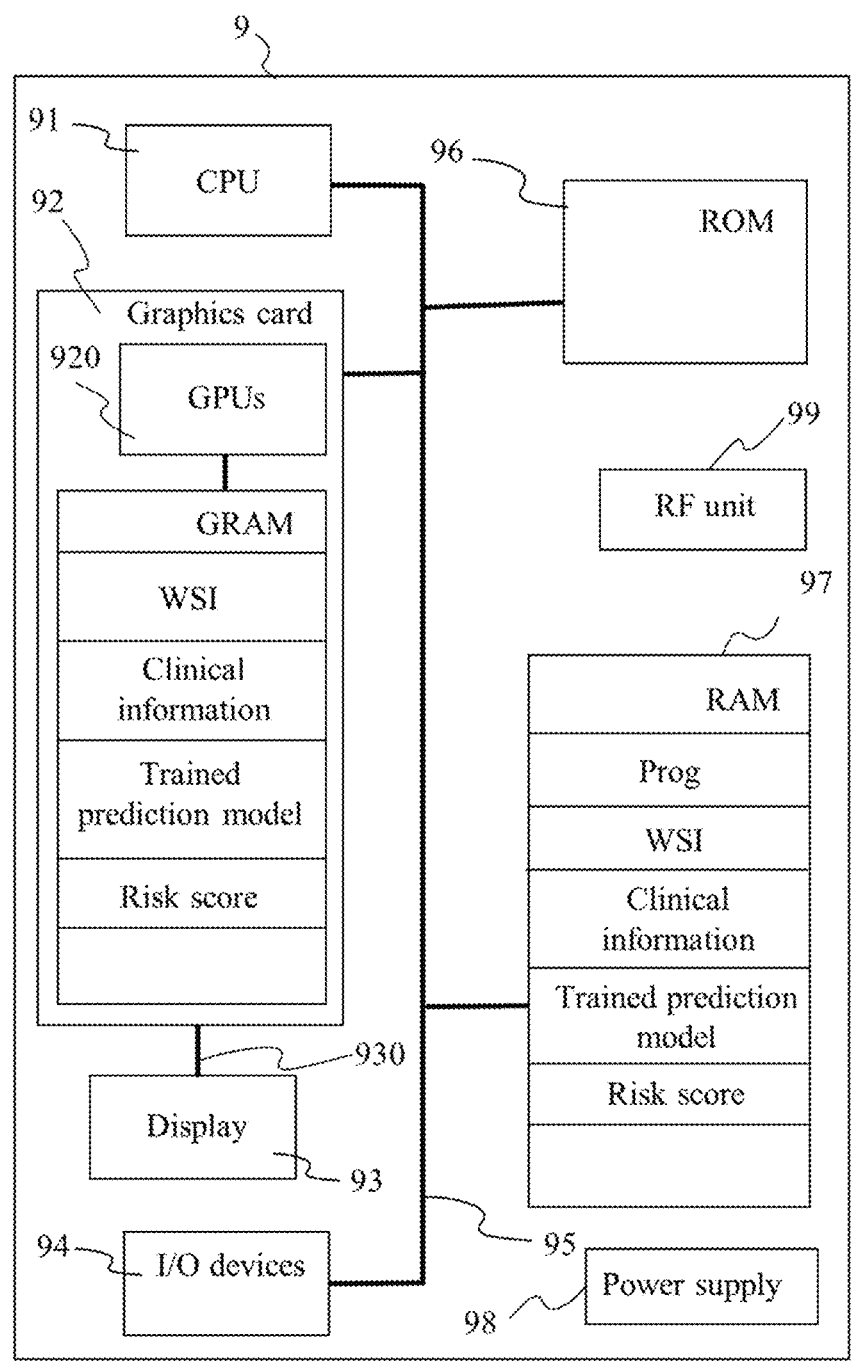
FIG. 4 shows an apparatus integrating the functions of the device for training of FIG. 1 and of the device for predicting of FIG. 3.

A particular apparatus 9, visible on FIG. 4, is embodying the device 1 as well as the device 6 described above. It corresponds for example to a workstation, a laptop, a tablet, a smartphone, or a head-mounted display (HMD).

That apparatus 9 is suited to output a risk score representative of a probability of relapse of said patient or representative of the health status of the patient and to related ML training. It comprises the following elements, connected to each other by a bus 95 of addresses and data that also transports a clock signal:
a microprocessor 91 (or CPU);
a graphics card 92 comprising several Graphical Processing Units (or GPUs) 920 and a Graphical Random Access Memory (GRAM); the GPUs are quite suited to image processing due to their highly parallel structure;
a non-volatile memory of ROM type 96;
a RAM 97;
one or several I/O (Input/Output) devices 94 such as for example a keyboard, a mouse, a trackball, a webcam;
a power source 98; and
a radiofrequency unit 99.

According to a variant, the power supply 98 is external to the apparatus 9.

The apparatus 9 also comprises a display device 93 of display screen type directly connected to the graphics card 92 to display synthesized images calculated and composed in the graphics card. The use of a dedicated bus to connect the display device 93 to the graphics card 92 offers the advantage of having much greater data transmission bitrates and thus reducing the latency time for training a prediction model configured to predict a relapse of a patient afflicted with cancer and for obtaining a risk score representative of a probability of relapse of said patient or representative of the health status of the patient. According to a variant, a display device is external to apparatus 9 and is connected thereto by a cable or wirelessly for transmitting the display signals. The apparatus 9, for example through the graphics card 92, comprises an interface for transmission or connection adapted to transmit a display signal to an external display means such as for example an LCD or plasma screen or a video-projector. In this respect, the RF unit 99 can be used for wireless transmissions.

It is noted that the word "register" used hereinafter in the description of memories RAM and GRAM can designate in each of the memories mentioned, a memory zone of low capacity (some binary data) as well as a memory zone of large capacity (enabling a whole program to be stored or all or part of the data representative of data calculated or to be displayed). Also, the registers represented for the RAM and the GRAM can be arranged and constituted in any manner, and each of them does not necessarily correspond to adjacent memory locations and can be distributed otherwise (which covers notably the situation in which one register includes several smaller registers).

When switched-on, the microprocessor 91 loads and executes the instructions of the program contained in the RAM 97.

As will be understood by a skilled artisan, the presence of the graphics card 92 is not mandatory, and can be replaced with entire CPU processing and/or simpler visualization implementations.

In variant modes, the apparatus 9 may include only the functionalities of the device 1, and not the functionalities of the device 6. In addition, the device 1 and/or the device 6 may be implemented differently than a standalone software, and an apparatus or set of apparatus comprising only parts of the apparatus 9 may be exploited through an API call or via a cloud interface.

One object of the present invention is a method for predicting a risk of relapse of a patient afflicted with cancer using a trained prediction device as described herein or using a trained prediction model obtained with the device as described herein or from the method as described herein.

Another object of the invention is a method for predicting the risk of relapse of a patient afflicted with cancer, said method comprising analyzing at least one whole histological slide image 23 comprising a representation of at least one portion of a cancerous tissue of the patient.

Analyzing at least one whole histological slide image 23 of the patient may comprise, using at least one processor:
  detecting cells in said at least one whole histological slide image 23 and associating each detected cell to a cell class representative of a cell status;
  segmenting tissues in said at least one whole histological slide image 23 and associating each segmented tissue to a tissue class representative of a tissue status;
  for each cell class, extracting at least one cell feature based on the cells detected for said cell class in the at least one whole histological slide image 23;
  for each tissue class, extracting at least one tissue feature based on the portion of the at least one whole histological slide image 23 relating to the segmented tissue associated to said tissue class;
  using said at least one cell feature and at least one tissue feature to predict the risk of relapse of a patient afflicted with cancer.

The method for predicting the risk of relapse as described herein does not comprise extracting a tissue sample for the patient. Furthermore, the method for predicting the risk of relapse as described herein does not comprise preparing the tissue previously extracted from the patient. As indicated above, the method for predicting the risk of relapse as described herein is implemented using at least one whole histological slide image 23 previously acquired.

In some embodiments, the method for predicting the risk of relapse as described herein is computer-implemented.

In some embodiments, the method is for predicting the risk of relapse of a patient afflicted with breast cancer. Said breast cancer may HR+/HER2⁻ breast cancer, in particular early invasive HR+/HER2⁻ breast cancer as defined herein.

Another object of present invention is a method for providing an adapted patient care to a cancer patient depending on their risk of relapse, said method comprising:
  determining whether the patient suffering from cancer is at low risk of relapse or not at low risk of relapse using a device for predicting a risk of relapse as described herein or using a trained prediction model obtained with the device as described herein or from the methods as described herein; and
  providing an adapted patient care to the cancer patient depending on their risk of relapse, said adapted patient care comprising surgery, radiotherapy, hormone therapy, chemotherapy, and/or an anti-relapse drug.

In particular, the adapted patient care is provided to the cancer patient depending on whether the cancer patient is determined to be at low risk of relapse or not at low risk of relapse.

For example, a patient not at low risk of relapse (or a patient determined to be not at low risk of relapse) may be a patient at high risk of relapse (or a patient determined to be at high risk of relapse).

In some embodiments, the method is thus for providing an adapted patient care to a cancer patient depending on their risk of relapse, said method comprising:
  determining whether the patient suffering from cancer is at low risk or at high risk of relapse using a device for predicting a risk of relapse as described herein or using a trained prediction model obtained with the device as described herein or from the methods as described herein; and
  providing an adapted patient care to the cancer patient depending on their risk of relapse, said adapted patient care comprising surgery, radiotherapy, hormone therapy, chemotherapy, and/or an anti-relapse drug.

Examples of surgery include tumor resection, lymph node surgery (such as sentinel lymph node biopsy, targeted axillary dissection, and/or axillary lymph node dissection), partial mastectomy (also known as lumpectomy) and total mastectomy.

Examples of radiotherapy include external beam radiation therapy (EBRT) and brachytherapy (also known as internal radiation therapy). Examples of external beam radiation therapy include whole breast radiation, accelerated partial breast irradiation, chest wall radiation, and lymph node radiation. Examples of brachytherapy includes intracavitary brachytherapy and interstitial brachytherapy.

Examples of hormone therapy (also known as endocrine therapy) include selective estrogen receptor modulators (SERMs) such as tamoxifen and toremifene; aromatase inhibitors (AIs) such as anastrozole, letrozole and exemestane; luteinizing hormone releasing hormone (LHRH) agonists or LH blockers, such as goserelin and leuprorelin; selective estrogen receptor degraders (SERDs) such as fulvestrant and elacestrant.

Example of chemotherapy include paclitaxel, 5-fluorouracil, docetaxel, epirubicin, carboplatin, capecitabine, eribulin, cyclophosphamide, and combinations thereof, in particular combinations of two or three of the listed chemotherapeutic agents. Examples of combinations of two chemotherapeutic agents include epirubicin and cyclophosphamide (EC), doxorubicin and cyclophosphamide (AC), and docetaxel and cyclophosphamide (TC).

As used herein, "anti-relapse drug" means a drug that is administered with the specific aim of preventing any type of relapse, such as a local relapse, a regional relapse, or a metastatic relapse. Examples of anti-relapse drugs include inhibitors of cyclin dependent kinase 4/6 (CDK4/6) also known as CDK4/6 inhibitors or CDK4/6i, and immunotherapy. Examples of CDK4/6 inhibitors include palbociclib, ribociclib, and abemaciclib. Examples of immunotherapy include nivolumab and pembrolizumab.

In some embodiments, the patient is determined to be at low risk of relapse and the adapted patient care comprises surgery, radiotherapy, hormone therapy and/or chemotherapy. For example, the chemotherapy may be adjuvant chemotherapy (i.e., administered after surgery) or neoadjuvant chemotherapy (i.e., administered before surgery).

The present invention thus also relates to a method for treating cancer in a patient determined to be at low risk of relapse, said method comprising:
  determining that the patient suffering from cancer is at low risk of relapse using a device for predicting a risk of relapse as described herein or using a trained prediction model obtained with the device as described herein or from the methods as described herein; and
  implementing an adapted patient care for the patient determined to be at low risk of relapse, said adapted patient care comprising surgery, radiotherapy, hormone therapy, and/or chemotherapy.

In some embodiments, the method for treating cancer in a patient determined to be at low risk of relapse comprises:
  determining that the patient suffering from cancer is at low risk of relapse using a device for predicting a risk of relapse as described herein or using a trained prediction model obtained with the device as described herein or from the methods as described herein; and
  implementing an adapted patient care for the patient determined to be at low risk of relapse, said adapted patient care comprising hormone therapy and/or chemotherapy (in particular adjuvant chemotherapy).

In some embodiments, implementing an adapted patient care for the patient determined to be at low risk of relapse does not comprise administering an anti-relapse drug to the patient determined to be at low risk of relapse. In other words, in some embodiments, implementing an adapted patient care for the patient determined to be at low risk of relapse excludes administering an anti-relapse drug to the patient determined to be at low risk of relapse. In some embodiments, implementing an adapted patient care for the patient determined to be at low risk of relapse consists of surgery, radiotherapy, hormone therapy, and/or chemotherapy. In some embodiments, implementing an adapted patient care for the patient determined to be at low risk of relapse consists of hormone therapy and chemotherapy, in particular adjuvant chemotherapy.

An adapted patient care provided to a patient determined to be at low risk of relapse may include radiotherapy, hormone therapy, and chemotherapy. An adapted patient care provided to a patient determined to be at low risk of relapse may include hormone therapy and chemotherapy, in particular adjuvant chemotherapy.

For example, an adapted patient care provided to a patient determined to be at low risk of relapse may include chemotherapy consisting of a combination of doxorubicin and cyclophosphamide (AC), followed or preceded by paclitaxel (for example either weekly or every two weeks), and hormonotherapy consisting of an aromatase inhibitor (for example administered for 2-3 years or for 5 years) or of tamoxifen (for example administered for 2-3 years or for 4.5-6 years).

In some embodiments, the patient is determined to be not at low risk of relapse (for example at high risk of relapse) and the adapted patient care comprises at least one of surgery, radiotherapy, hormone therapy and chemotherapy, and an anti-relapse drug.

The present invention thus also relates to a method for treating cancer in a patient determined to be not at low risk of relapse (for example at high risk of relapse), said method comprising:
  determining that the patient suffering from cancer is not at low risk of relapse (for example at high risk of relapse) using a device for predicting a risk of relapse as described herein or using a trained prediction model obtained with the device as described herein or from the methods as described herein; and
  implementing an adapted patient care for the patient determined to be not at low risk of relapse (for example at high risk of relapse), said adapted patient care comprising at least one of surgery, radiotherapy, hormone therapy and chemotherapy, and an anti-relapse drug.

In some embodiments, the method for treating cancer in a patient determined to be not at low risk of relapse (for example at high risk of relapse) comprises:
  determining that the patient suffering from cancer is not at low risk of relapse (for example at high risk of relapse) using a device for predicting a risk of relapse as described herein or using a trained prediction model obtained with the device as described herein or from the methods as described herein; and
  implementing an adapted patient care for the patient determined to be not at low risk of relapse (for example at high risk of relapse), said adapted patient care comprising hormone therapy, chemotherapy (in particular adjuvant chemotherapy), and an anti-relapse drug.

In some embodiments, implementing an adapted patient care for the patient determined to be not at low risk of relapse (for example at high risk of relapse) comprises or consists of surgery, radiotherapy, hormone therapy, chemotherapy, and an anti-relapse drug. In some embodiments, implementing an adapted patient care for the patient determined to be not at low risk of relapse (for example at high risk of relapse) comprises or consists of hormone therapy, chemotherapy (in particular adjuvant chemotherapy), and an anti-relapse drug.

An adapted patient care provided to a patient determined to be not at low risk of relapse (for example at high risk of relapse) may include radiotherapy, hormone therapy, chemotherapy, and an anti-relapse drug such as a CDK4/6 inhibitor. An adapted patient care provided to a patient determined to be not at low risk of relapse (for example at high risk of relapse) may include hormone therapy, chemotherapy (in particular adjuvant chemotherapy), and an anti-relapse drug such as a CDK4/6 inhibitor.

For example, an adapted patient care provided to a patient determined to be not at low risk of relapse (for example at high risk of relapse) may include (i) chemotherapy consisting of a combination of doxorubicin and cyclophosphamide (AC), followed or preceded by paclitaxel (for example either weekly or every two weeks), (ii) hormonotherapy consisting of an aromatase inhibitor such as anastrozole or letrozole, and (iii) an anti-relapse drug consisting of the CDK4/6 inhibitor abemaciclib. Another example of an adapted patient care provided to a patient determined to be not at low risk of relapse (for example at high risk of relapse) may include (i) chemotherapy consisting of a combination of doxorubicin and cyclophosphamide (AC), followed or preceded by paclitaxel (for example either weekly or every two weeks), (ii) hormonotherapy consisting of an aromatase inhibitor (such anastrozole, letrozole, or exemestane) or of a LH blocker (such as goserelin or leuprorelin), and (iii) an anti-relapse drug consisting of the CDK4/6 inhibitor ribociclib.

In some embodiments, the cancer patient is a breast cancer patient. Said breast cancer may HR+/HER2⁻ breast cancer, in particular early invasive HR+/HER2⁻ breast cancer.

A patient suffering from early invasive HR+/HER2− breast cancer may be defined as a breast cancer patient with lymph node involvement (that is to say a breast cancer patient in whom cancer cells are present in one or several nearby lymph node(s)). In particular, a patient suffering from early invasive HR+/HER2− breast cancer may be defined as a breast cancer patient with at least 4 positive lymph nodes (that is to say 4 lymph nodes in which cancer cells are present) or with 1 to 3 positive lymph node(s) and one of the following: grade 3 tumor, tumor size ≥50 mm, or Ki67≥20%.

For the cancer patient as described herein, a low risk of relapse or being at low risk of relapse may be defined as a low probability of suffering from any type of relapse (e.g., local, regional, or metastatic) within 5 years from the date of cancer diagnosis, the date of biopsy, the date of treatment initiation, or the date or surgery. A low risk of relapse or being at low risk of relapse may be defined as a low probability of suffering from any type of relapse (e.g., local, regional, or metastatic) within 10 years from the date of cancer diagnosis, the date of biopsy, the date of treatment initiation, or the date or surgery, with a treatment comprising surgery, radiotherapy, hormone therapy, and/or chemotherapy and excluding an anti-relapse drug, such as a CDK4/6 inhibitor.

In some embodiments, a cancer patient at low risk of relapse as described herein (i.e., a cancer patient having a low risk of relapse) is a cancer patient having a relative risk score lower than 0.2 (<0.2), corresponding to an absolute risk score lower than −0.7 (<−0.7), the risk score (relative or absolute) being obtained with one of the devices and/or methods as described herein.

In some embodiments, a cancer patient not at low risk of relapse as described herein (i.e., a cancer patient not having a low risk of relapse, such as a patient at high risk of relapse) is a patient having a relative risk score equal to or greater than 0.2 (≥0.2), corresponding to an absolute risk score equal to or greater than −0.7 (>−0.7), the risk score (relative or absolute) being obtained with one of the devices and/or methods as described herein.

EXAMPLES

The present invention is further illustrated by the following examples.

Example 1

Materials and Methods

The following section provide an example of implementation of the algorithm(s) (i.e., methods for training and predicting) for obtaining the risk score, which comprises several sequential steps i.e., 1) obtaining annotations of cells and tissue, 2) extracting feature values from mathematical formula applied on these annotations, and 3) computing a probability of relapse (i.e., one example of risk score) from said extracted values.

1. Annotations of Histological Images

1.A. Annotations of all Cells

This first step aims at detecting every single cell in a whole histological slide image, and assigning each cell to one of 4 classes i.e. i) tumor, ii) connective, iii) inflammatory, iv) normal epithelial. A Fully Convolutional One-Stage Object Detection (FCOS) model was trained using manually-curated ground-truth annotations from 400 512*512 pixels patches of breast cancer at 40×. The Applicant used the ResNet50 architecture pre-trained on ImageNet as the backbone model. Both classification and regression heads comprised four ReLU-activated convolutional layers of kernel size 3 and stride 1, with batch normalization. Contrary to the original implementation of FCOS, image rescaling was discarded to input patches with the same magnification as the model. Data augmentation consisted of rotations, flips, shifts, and color jitter. For each input patch, the same data augmentation was performed to the associated ground-truth bounding boxes using the Albumentations python library version 1.2.1. The detection model parameters were stochastically updated using the Adam optimizer from errors computed by the focal loss cost function with a learning rate of 10-4, a regularization of 10-4 and a batch size of four patches. Training was conducted for up to 2000 epochs on an A40 GPU.

1.b. Annotations of Tissues

This second step aims at detecting and classifying every single pixel in a whole histological slide image in one of 7 classes i.e. i) tumor, ii) tumor stroma, iii) inflammatory, iv) in-situ tumor, v) benign gland, vi) necrosis, or vii) the rest. A U-Net model was trained using manually-curated ground-truth annotations from 1500 1024*1024 pixels patches of breast cancer at 20×. The U-Net model had a depth of 4, and an attention mechanism was employed in the output decoding blocks. The Applicant used the MobileNet-v3-large architecture pre-trained on ImageNet as the backbone model. For each input patch, the same data augmentation was performed to the associated ground-truth bounding boxes using the Albumentations python library version 1.2.1. The detection model parameters were stochastically updated using the Adam optimizer from errors computed by the focal loss cost function with a learning rate of 10-4, a regularization of 10-4 and a batch size of eight patches. Training was conducted for up to 10000 epochs on an A40 GPU.

2. Feature Extraction

For each whole histological slide image, the same mathematical formulas are computed from the previously obtained annotations, resulting in feature values. The following table synthesizes the categories of extracted features:

| Feature class name | Description | Number of features |
| --- | --- | --- |
| Cell count | For each cell detection class (i.e. 4 classes), count of the number of detected cells of this class in the following regions: The complete tissue, i.e. the whole histological slide image without non-tissue areas Each of the 7 detected tissue classes | 32 = 4 classes * 8 regions |

-continued

| Feature class name | Description | Number of features |
|---|---|---|
| Cell density | For each cell detection class (i.e. 4 classes), count of the number of detected cells divided by the total number of pixels in the following regions:<br>The complete tissue, i.e. the whole histological slide image without non-tissue areas<br>Each of the 7 detected tissue classes | 32 = 4 classes * 8 regions |
| Paired proportion | For each pair of cell detection class (i.e. 4 classes, i.e. 12 pairs), ratio of the number of detected cells of the first class of the pair over the number of detected cells of the second class of the pair, in the following regions:<br>The complete tissue, i.e. the whole histological slide image without non-tissue areas<br>Each of the 7 detected tissue classes | 94 = 12 pairs of classes * 8 regions |
| Relative proportion | For each cell detection class (i.e. 4 classes), count of the number of detected cells of this class divided by the total number of detected cells in the following regions:<br>The complete tissue, i.e. the whole histological slide image without non-tissue areas<br>Each of the 7 detected tissue classes | 32 = 4 classes * 8 regions |
| Spatiality of tissue regions | For each tissue segmentation class (i.e. 7 classes), computation of the following morphological formulas:<br>Eccentricity<br>Major axis length<br>Minor axis length<br>Perimeter<br>Area<br>Perimeter divided by area<br>Solidity<br>Convex area<br>Spread<br>Extent | 70 = 7 classes * 10 morphological formulas |
| Spatiality of tissue nests | For each tissue segmentation class (i.e. 7 classes), identification of contiguous regions within the whole slide image of this class - these are denoted as "nest".<br>Extraction of a first set of features i.e.:<br>Count of nests<br>Count of nests over the total segmented pixels of the associated segmentation class<br>Count of nests over the total segmented pixels of tissue<br>Then, for each nest, computation of all 10 features from the feature class "SPATIALITY OF TISSUE REGIONS", resulting in 10 x the number of nests of the considered class features. Then, computation of the following mathematical descriptors on this latter list of features, per morphological feature:<br>Mean<br>Percentiles 25%, 50% (i.e. median) and 75%<br>Largest value (i.e. max) for the nest with largest area | 511 = (7 classes * 3 count-based features) + (7 classes * 10 morphological features * 7 mathematical descriptors) |

-continued

| Feature class name | Description | Number of features |
|---|---|---|
| Size descriptors of cells | Mean of the 5 values for the 5 nests with largest area<br>Mean of the 20 values for the 20 nests with largest area<br>For each tissue type class (i.e. 7 classes from segmentation, + the whole tissue), for each cell detection class (i.e. 4 classes), computation of the following descriptors for each cell:<br>Area (of the detected bounding box)<br>Size of the largest length<br>Size of the lowest length<br>Then, computation of the following descriptors from all cells of each cell detection class of each tissue type:<br>Mean<br>Standard deviation<br>Mean of the size of the lowest length over the size of the largest length<br>Standard deviation of the size of the lowest length over the size of the largest length | 128 = 8 tissue types * 4 cell detection class * 4 descriptors |

After this step, each whole histological slide image is therefore synthesized into 899 values.

3. Predicting a Probability of Relapse/a Risk Score 3. a. Data

A cohort of 350 patients was used to train and validate the risk score representative of a probability of relapse of said patient. Each patient had:

Clinico-pathological data including age, grade of the tumor computed by a pathologist (1, 2 or 3), Ki67 estimates computed by a pathologist, progesterone receptor positivity computed by a pathologist (positive or negative), menopausal status (yes or no), number of positive lymph nodes, and tumor size computed by a pathologist (in mm);

One whole histological slide image stained with HE (hematoxylin and eosin) or HES (hematoxylin, eosin, and safranin);

Follow-up data including dates of diagnosis, distant relapse (or not applicable-NA), local relapse (or NA), regional relapse (or NA), death (or NA), and last follow-up without any event.

These patients have all been treated in 2012 with the due standard of care, and had non-metastatic breast cancers with the molecular class HR+/HER2−(i.e. were diagnosed with non-metastatic breast cancers with the molecular class HR+/HER2−).

3. b. Model

A Cox model was trained in a 5-fold cross-validation fashion with 2 repeats. This model predicts an absolute risk of relapse ranging from −infinity to +infinity. It is trained to rank patients, from the previously extracted features, such that patients are ranked in ascending orders of risk compared to their risk of developing a relapse, which was defined as any type of relapse (local, regional, or metastatic)—this model is also able to take into account censorship from patients without events. The model comprised 1 parameter per input extracted histological feature plus 1 parameter per clinical feature plus 1 intercept parameter, resulting in a 908-parameter model. A combination of L1 and L2 regularizations were employed, with values of 1 and 0.1 respectively. The final model was obtained by ensembling the 10 trained models (=5 folds*2 repeats).

Results

The obtained risk score can predict the risk of relapse with an AUC of 0.82 when measuring the relapse prediction at a timestep of 5 years.

For patients with early invasive HR$^+$/HER2 breast cancer, with lymph node involvement and at least one of the following conditions:

Looking at patients with the following clinical features:
At least 4 positive lymph nodes
Or between 1 and 3 positive lymph nodes and:
  Grade 3
  Or tumor size >=50 mm
  Or Ki67 >=20%, with a cutoff of −0.7 of the predicted absolute risk (corresponding to a cut-off of 0.2 of the predicted relative risk), the risk score allowed to identify a group of 20% of such patients with no relapse at 5 years, 20% being the rate of the patients who indeed did not relapse at 5 years. The patients thus identified as being at low risk of relapse were the patients with an absolute risk score lower than −0.7 (<−0.7), corresponding to a relative risk score lower than 0.2 (<0.2). Conversely, the patients with an absolute risk score equal to or greater than −0.7 (>−0.7), corresponding to a relative risk score equal to or greater than 0.2 (>0.2), were determined to be not at low risk of relapse.

Example 2

Approximately 70% of breast cancers are hormone-sensitive (i.e. HR+/HER2−). In particular, 20% of these cancers induce metastatic relapse which greatly reduce patient survivability. Chemotherapy is not systematically proposed for their treatment because of its toxic effect and a therapeutic relevance that is currently difficult to predict due to the exacerbated heterogeneity of breast cancers. Although there are commercial solutions predictive of metastatic relapse, these solutions suffer from several limitations: their effectiveness is not clear for patients at moderate risk; they do not apply to all types of BC; and they are expensive and may not be reimbursed by insurers. Therefore, there is a need for an innovative metastatic relapse prediction solution (i.e. biomarker, test) for BC that is robust, holistic, inexpensive, and easily applicable.

Indeed, the obtained risk score representative of a probability of relapse of the patient or representative of the health status of the patient, as disclosed in this invention, can be utilized to make decisions regarding the administration of medication to the patient, either escalating or de-escalating treatment, meaning adding or removing a specific type of medication. Typically, patients receive both the standard of care (i.e., surgery, radiotherapy, hormone therapy and/or chemotherapy) and an anti-relapse drug, such as a CDK4/6 inhibitor, as standard practice. However, for certain patients, anti-relapse drugs may have no effect or small effect on preventing relapse, allowing for a reduction to the standard of care alone to limit toxicity. This is particularly interesting in patients meeting specific criteria (e.g., presence of cancer cells in the lymph nodes around the tumor).

The invention claimed is:

1. A device for training a prediction model configured to predict a risk of relapse of a patient afflicted with cancer, wherein the device comprises:
   at least one input configured to receive a set of data from a plurality of subjects, each subject of said plurality of subjects having received a previous diagnosis for said cancer, wherein said set of data for each subject comprises:
      at least one whole histological slide image, said image comprising a representation of at least one portion of a cancerous tissue of said subject;
      clinical information associated to the subject, said clinical information comprising at least a subject health status evaluated subsequently to said previous diagnosis of said cancer;
   at least one processor configured to:
      define a training dataset comprising a plurality of training samples by, for each subject of the plurality of subjects:
         detecting cells in the at least one whole histological slide image of said subject and associating each detected cell to a cell class representative of a cell status;
         segmenting tissues in the at least one whole histological slide image of said subject and associating each segmented tissue to a tissue class representative of a tissue status;
         for each cell class, extracting at least one cell feature based on the cells detected for said cell class in the at least one whole histological slide image of said subject;
         for each tissue class, extracting at least one tissue feature based on the portion of the at least one whole histological slide image of said subject relating to the segmented tissue associated to said tissue class;
         defining one training sample as comprising said at least one cell feature, said at least one tissue feature and said subject health status associated to the subject;
      train a prediction model using said defined training dataset, wherein the prediction model is configured to receive as input at least one cell feature and at least one tissue feature for a patient, said at least one cell feature and at least one tissue feature being extracted from at least one whole histological slide image said image comprising a representation of at least one portion of a cancerous tissue of said patient and providing as output a risk score representative of a probability of relapse of said patient or representative of the health status of the patient;
   at least one output configured to provide said trained prediction model.

2. The device according to claim 1, wherein the prediction model is a Cox model.

3. The device according to claim 2, wherein the prediction model is trained using a 5-fold cross-validation scheme.

4. The device according to claim 1, wherein detecting cells in a whole histological slide image and associating each detected cell to a cell class is performed by a convolutional neural network.

5. The device according to claim 1, wherein segmenting tissues in a whole histological slide image and associating each segmented tissue to a tissue class is performed by a convolutional neural network configured to class each pixel of the whole histological slide image into one tissue class among a plurality of predefined tissue classes.

6. The device according to claim 1, wherein extracting at least one tissue feature comprises:
   for each tissue class, identifying nests, being two contiguous segmented tissues portions within the whole slide image, each of said two segmented tissues portions being associated with said tissue class;
   extracting at least one tissue feature based on the identified nests in the whole slide image, and/or
   for each identified nest, extracting at least one tissue feature being a morphological feature.

7. The device according to claim 1, wherein extracting at least one cell feature comprises:
   for each tissue class, selecting cells comprised in the associated segmented tissues;
   for each cell class, for each selected cell associated to said cell class, computing at least one feature being a morphological feature; and/or
   for a group of cells associated to a same cell class and selected for a same tissue class, extract at least one feature being a statistical feature computed using said group of cells.

8. The device according to claim 1, wherein the cancer is a breast cancer, the clinical information associated to one subject is comprised in the training sample, the prediction model is configured to receive as input at least one clinical information associated to the subject and the clinical information further comprises at least one of the following: tumor size, menopausal status, grade of the tumor, progesterone receptor positivity, Ki67 protein estimation as a percentage, number of positive lymph nodes, the presence of micrometastases only in lymph nodes, age at diagnosis, percentage of cells positive to the progesterone receptor, intensity of the progesterone receptor, estrogen receptor positivity, percentage of cells positive to the estrogen receptor, intensity of the estrogen receptor, human epidermal growth factor receptor 2 positivity, percentage of cells positive to the human epidermal growth factor receptor 2, intensity of the human epidermal growth factor receptor 2, the mutational status of BRCA1, the mutational status of BRCA2, type of surgery, residual tumor classification, histology tumor type, pathological T stage, pathological N stage, pathological M stage, type of treatments received and duration of treatments received.

9. A device for predicting a risk of relapse of a patient afflicted with cancer using a trained prediction model obtained from the device according to claim 1, said device comprising:
- at least one input configured to receive at least one whole histological slide image said image comprising a representation of at least one portion of a cancerous tissue of said patient;
- at least one processor configured to:
  - detect cells in the at least one whole histological slide image of said patient and associate each detected cell to a cell class representative of a cell status;
  - segment tissues in the at least one whole histological slide image of said patient and associate each segmented tissue to a tissue class representative of a tissue status;
  - for each cell class, extract at least one cell feature based on the cells detected for said cell class in the at least one whole histological slide image of said patient;
  - for each tissue class, extract at least one tissue feature based on the portion of the at least one whole histological slide image of said patient relating to the segmented tissue associated to said tissue class;
  - provide as input to said trained prediction model said at least one cell feature and at least one tissue feature, obtaining a risk score representative of a probability of relapse of said patient or representative of the health status of the patient;
- at least one output configured to provide said risk score.

10. The device according to claim 9, the device is further configured to receive as input clinical information associated to the patient, said patient clinical information comprising at least one of the following: tumor size, menopausal status, grade of the tumor, progesterone receptor positivity, Ki67 protein estimation as a percentage, number of positive lymph nodes, the presence of micrometastases only in lymph nodes, age at diagnosis, percentage of cells positive to the progesterone receptor, intensity of the progesterone receptor, estrogen receptor positivity, percentage of cells positive to the estrogen receptor, intensity of the estrogen receptor, human epidermal growth factor receptor 2 positivity, percentage of cells positive to the human epidermal growth factor receptor 2, intensity of the human epidermal growth factor receptor 2, the mutational status of BRCA1, the mutational status of BRCA2, type of surgery, residual tumor classification, histology tumor type, pathological T stage, pathological N stage, pathological M stage, type of treatments received and duration of treatments received.

11. A device for predicting a response to cancer treatment of a patient using a trained prediction model obtained from the device according to claim 1, said device for predicting a response to cancer treatment comprising:
- at least one input configured to receive at least one whole histological slide image of said patient;
- at least one processor configured to:
  - detect cells in the at least one whole histological slide image of said patient and associating each detected cell to a cell class representative of a cell status;
  - segment tissues in the at least one whole histological slide image of said patient and associating each segmented tissue to a tissue class representative of a tissue status;
  - for each cell class, extract at least one cell feature based on the cells detected for said cell class in the at least one whole histological slide image of said patient;
  - for each tissue class, extract at least one tissue feature based on the portion of the at least one whole histological slide image of said patient relating to the segmented tissue associated to said tissue class;
  - provide as input to said trained prediction model said at least one cell feature and at least one tissue feature, obtaining a risk score representative of a probability of relapse of said patient or representative of the health status of the patient;
  - use said risk score for predicting a response to cancer treatment of the patient;
- at least one output configured to provide said response to cancer treatment of the patient.

12. A computer-implemented method for training a prediction model to predict a relapse of a patient afflicted with cancer, said method for training a prediction model comprising:
- receiving a set of data from a plurality of subjects, each subject of said plurality of subjects having received a previous diagnosis for said cancer, wherein said set of data for each subject comprises:
  - at least one whole histological slide image, said image comprising a representation of at least one portion of a cancerous tissue of said subject;
  - clinical information associated to the subject, said clinical information comprising at least a subject health status evaluated subsequently to said previous diagnosis of said cancer;
- defining a training dataset comprising a plurality of training samples by, for each subject of the plurality of subjects:
  - detecting cells in the at least one whole histological slide image of said subject and associating each detected cell to a cell class representative of a cell status;
  - segmenting tissues in the at least one whole histological slide image of said subject and associating each segmented tissue to a tissue class representative of a tissue status;
  - for each cell class, extracting at least one cell feature based on the cells detected for said cell class in the at least one whole histological slide image of said subject;
  - for each tissue class, extracting at least one tissue feature based on the portion of the at least one whole histological slide image of said subject relating to the segmented tissue associated to said tissue class;
  - defining one training sample as comprising said at least one cell feature, said at least one tissue feature and said subject health status associated to the subject;
- training a prediction model using said defined training dataset, wherein the prediction model is configured to receive as input at least one cell feature and at least one tissue feature for a patient, said at least one cell feature and at least one tissue feature being extracted from at least one whole histological slide image said image comprising a representation of at least one portion of a cancerous tissue of said patient and providing as output a risk score representative of a probability of relapse of said patient or representative of the health status of the patient;
- outputting said trained prediction model.

13. The method according to claim 12, wherein said cancer is a breast cancer, the clinical information associated to one subject is comprised in the training sample, the prediction model is configured to receive as input at least one clinical information associated to the subject and the clinical information further comprises at least one of the following: tumor size, menopausal status, grade of the tumor, progesterone receptor positivity, Ki67 protein estimation as a percentage, number of positive lymph nodes, the presence of micrometastases only in lymph nodes, age at diagnosis, percentage of cells positive to the progesterone receptor, intensity of the progesterone receptor, estrogen receptor positivity, percentage of cells positive to the estrogen receptor, intensity of the estrogen receptor, human epidermal growth factor receptor 2 positivity, percentage of cells positive to the human epidermal growth factor receptor 2, intensity of the human epidermal growth factor receptor 2, the mutational status of BRCA1, the mutational status of BRCA2, type of surgery, residual tumor classification, histology tumor type, pathological T stage, pathological N stage, pathological M stage, type of treatments received and duration of treatments received.

14. A non-transitory program storage device comprising instructions which, when executed by a computer, cause the computer to carry out the method of claim 12.

15. A method for treating cancer in a patient determined to be at low risk of relapse, said method comprising:
   determining that the patient suffering from cancer is at low risk of relapse by:
      receiving at least one whole histological slide image said image comprising a representation of at least one portion of a cancerous tissue of said patient;
      detecting cells in the at least one whole histological slide image of said patient and associate each detected cell to a cell class representative of a cell status;
      segmenting tissues in the at least one whole histological slide image of said patient and associate each segmented tissue to a tissue class representative of a tissue status;
      for each cell class, extracting at least one cell feature based on the cells detected for said cell class in the at least one whole histological slide image of said patient;
      for each tissue class, extracting at least one tissue feature based on the portion of the at least one whole histological slide image of said patient relating to the segmented tissue associated to said tissue class;
      providing as input to said trained prediction model said at least one cell feature and said at least one tissue feature, obtaining a risk score representative of a probability of relapse of said patient or representative of the health status of the patient;
   outputting said risk score;
   determining that the patient is at low risk of relapse; and
   implementing an adapted patient care for the patient determined to be at low risk of relapse, said adapted patient care comprising hormone therapy and/or chemotherapy.

16. A method for treating cancer in a patient determined to be at low risk of relapse, said method comprising:
   determining that the patient suffering from cancer is at low risk of relapse by analyzing at least one whole histological slide image comprising a representation of at least one portion of a cancerous tissue of the patient, wherein analyzing said at least one whole histological slide image comprises, using at least one processor:
      detecting cells in said at least one whole histological slide image and associating each detected cell to a cell class representative of a cell status;
      segmenting tissues in said at least one whole histological slide image and associating each segmented tissue to a tissue class representative of a tissue status;
      for each cell class, extracting at least one cell feature based on the cells detected for said cell class in the at least one whole histological slide image;
      for each tissue class, extracting at least one tissue feature based on the portion of the at least one whole histological slide image relating to the segmented tissue associated to said tissue class; and
      using said at least one cell feature and at least one tissue feature to predict the risk of relapse of the patient suffering from cancer; and
   implementing an adapted patient care for the patient determined to be at low risk of relapse, said adapted patient care comprising hormone therapy and/or chemotherapy.

17. The method according to claim 16, wherein said cancer is breast cancer.

18. The method according to claim 17, wherein said breast cancer is HR$^+$/HER2$^-$ breast cancer.

* * * * *